(12) United States Patent
Kawasaki

(10) Patent No.: US 6,794,190 B2
(45) Date of Patent: Sep. 21, 2004

(54) METHOD FOR PRODUCING A TRANSFORMED PLANT WITH A HIGH CAPACITY BINARY SHUTTLE VECTOR

(75) Inventor: Shinji Kawasaki, Ibaraki (JP)

(73) Assignee: National Institute of Agrobological Sciences, Tsukuba (JP)

( * ) Notice: Subject to any disclaimer, the term of this patent is extended or adjusted under 35 U.S.C. 154(b) by 0 days.

(21) Appl. No.: 10/223,757

(22) Filed: Aug. 20, 2002

(65) Prior Publication Data

US 2003/0003585 A1 Jan. 2, 2003

Related U.S. Application Data

(62) Division of application No. 09/641,169, filed on Aug. 17, 2000, now Pat. No. 6,521,408, which is a division of application No. 08/937,902, filed on Sep. 25, 1997, now Pat. No. 6,165,780.

(30) Foreign Application Priority Data

Sep. 26, 1996 (JP) .............................................. 8-255184

(51) Int. Cl.$^7$ .............................................. C12N 15/82
(52) U.S. Cl. ....................................................... 435/468
(58) Field of Search .............................. 435/320.1, 468; 536/23.1; 800/295

(56) References Cited

U.S. PATENT DOCUMENTS 5,614,395 A 3/1997 Ryals
6,165,780 A * 12/2000 Kawasaki ................ 435/320.1

OTHER PUBLICATIONS

Wardhan, H. et al., Molecular Analysis of the RecA gene of Agrobacterium tumefaciens C58, Gene, vol. 121, p. 133–138 (1992).
Riera et al., Interspecies regulation of the recA gene of gram–negative bacteria lacking an E. coli–like SOS operator, Mol. Gen. Genet, vol. 245, p. 523–527 (1994).
Hiei, Y., et al., Efficient Transformation of rice (Oryza sativa L.) Mediated by Agrobacterium and sequence analysis of the boundaries of the T–DNA, The Plant Journal vol. 6, No. 2, pp. 271–282 (1994).
Bhattacharyya, M. et al., Reduced variation in transgene expression from a binary vector with selectable markers at the right and left T–DNA borders, The Plant Journal vol. 6, No. 6, pp. 957–968 (1994).
van Engelen, F., et al., pBINPLUS: an improved plant transformation vector based on pBIN 19, Transgenic Research vol. 4, No. 4, pp. 288–290 (1995).
Farrand, S., et al., Construction of an Agrobacterium tumefaciens C58 recA Mutant, Journal of Bacteriology, vol. 171, No. 10, Oct. 1989, pp. 5314–5321.
Olszewski, et al., "Specialized binary vector for plant transformation: expression of the Arabidopsis thaliana AHAS gene in Nicotiana tabacum", Nucleic Acids Research, vol. 16, No. 22, 1988, pp 10765–10782.

* cited by examiner

Primary Examiner—Terry McKelvey
(74) Attorney, Agent, or Firm—Davidson, Davidson & Kappel, LLC

(57) ABSTRACT

The invention provides a high capacity binary shuttle vector having T-DNA region and Ri ori and capable to integrate a large genome fragment in it; a genomic library having the ability to transform a plant, especially monocotyledonous ones; a plant transformed with the high capacity binary shuttle vector; and a method of searching for a useful gene by use of the above vector. The present high capacity binary shuttle vector can introduce a large genome fragment of 10 kb or more, easily, efficiently and stably into a plant, especially monocotyledonous ones under those conditions in which the rearrangement or deletion of these genome fragments does not occur. The invention also provides some other vectors derived from the above Ri ori driven vectors, which can integrate circular genome library plasmids with a lox site, or which can efficiently transform plants with genes of arbitrary expression properties. The invention includes also the assessment method for the functions of genome fragments inserted in the above vectors by complementation assay. In addition, a useful gene or gene complex can be efficiently examined so its isolation is also made easy.

3 Claims, 6 Drawing Sheets

1. pBIGRZ 1
2. pBIGRZ 2 pBIGZ

METHOD FOR PRODUCING A TRANSFORMED PLANT WITH A HIGH CAPACITY BINARY SHUTTLE VECTOR

This application is a divisional of U.S. patent application Ser. No. 09/641,169, filed Aug. 17, 2000, now U.S. Pat. No. 6,521,408, which is a divisional of U.S. patent application Ser. No. 08/937,902, filed Sep. 25, 1997, now U.S. Pat. No. 6,165,780.

FIELD OF THE INVENTION

The present invention relates to a high capacity binary shuttle vector for plant transformation, etc. In particular, the present invention relates to a high capacity binary shuttle vector which is used for seed plants transformation, particularly monocotyledonous plants which were difficult to transform in spite of their economical importance, but it is also used very powerfully for the complementation test analysis of genome functions and the construction of a genome library for genome function analysis.

BACKGROUND OF THE INVENTION

Monocotyledonous plants are more difficult to transform than dicotyledonous plants, in spite of their importance in agriculture. The conventional transformation of these plants has been carried out by various forced introduction methods such as those using gene guns for intact cells, or electroporation or PEG (polyethylene glycol) method for protoplasts.

However, there are problems in the electroporation method or PEG method that regeneration from protoplasts to normal plants is difficult, and in case of gene gun, that expensive facilities are required and a large number of samples can not be processed simultaneously. Furthermore, a large gene fragment of 10 kb or more into monocotyledonous plants has not been introduced without its rearrangement.

Recently, Hiei et al. have reported that rice, a typical monocotyledonous crop can be transformed with a pBI system vector and Agrobacterium (Hiei et al., Plant Journal, 6:271–282 (1994)). This has made the transformation of rice drastically easy.

However, the pBI vector used by Hiei et al. can stably introduce only about 10 kb DNA into rice. If larger DNA was integrated into such a shuttle vector, the vector could not be stably maintained even in E. coli.

By the recent advances of genome studies, the positional cloning method to isolate a gene, which is based on its positional information on the chromosome map, became the focus of interest as a promising method to isolate the useful gene determining agricultural traits. In order to apply this technique to identify genes causing these traits from the candidate genes selected by using their map information, the trait expression by the gene in the genome fragment must be confirmed by transformation of the fragment to plant. In this case, introduction of the larger genome fragment makes the screening of genes the more efficient. Therefore, it is desirable to introduce as large a genome fragment as possible.

Although the binary cosmid method and PEG method are known to introduce genome fragments of 10 kb or larger size into a plant, both of the methods have deficiencies as follows:

(1) As for the binary cosmid method, the upper size of a genome fragment to be introduced is limited up to about 20 kb, and pBI system RK2 is used as replication origin. Therefore, it has been often difficult to stably maintain the plasmid even in E. coli into which the plasmid with the chromosome fragment is to be introduced at first.

(2) As for the PEG method, the regeneration from protoplasts requires high proficiency of the skill, and often the introduced fragments are severely rearranged making normal complementation by the fragment rather difficult. Therefore, such methods are not sufficiently suited to assay the functions of large genome fragments.

SUMMARY OF THE INVENTION

The present invention was made in view of the circumstances described above. The object of the present invention is to introduce a genomic DNA fragment of 10 kb or larger size into plants, particularly higher plants. And it can be also used to monocotyledonous plants which are difficult to transform although many of them are agriculturally important.

Another objective of the present invention is to establish an efficient and stable complementation analysis method for a genome region of 10 kb or larger than that, which is very difficult to be introduced into plants by conventional methods. By introducing such a large genome fragment efficiently to plants, isolation of the genes controlling various agricultural traits can be more efficient. Another object of this invention is to introduce a large gene complex into a plant as a block to enable them to express complicated traits in plants. Sometimes such gene complex is located in a group as an operon.

That is, the present invention relates to a high capacity binary shuttle vector comprising T-DNA region, and Ri replication origin.

The high capacity binary shuttle vector of the present invention is a binary shuttle vector.

Further, said high capacity shuttle vector comprises a gene with a multi-cloning site in the T-DNA region, specifically lacZ gene.

Further, said high capacity binary shuttle vector comprises some or an antibiotic resistant genes being introduced between the lacZ gene introduced in the T-DNA region and the border regions of the T-DNA. Said border region is preferably a left border region, and said antibiotic resistance gene is preferably a hygromycin resistant gene.

Another selection marker antibiotic resistance can be kanamycin resistance gene which can be used as a selection marker in E. coli, and dicotyledonous plants.

Further, said high capacity shuttle vector may integrate a fragment with various sizes ranging from a small DNA fragment to a large genome fragment in it. It is confirmed that the genome fragments sized up to at least 40 kb can be efficiently integrated to rice, and larger size of it may be possible to be integrated.

The present invention is a binary vector comprising a lox site in T-DNA region, a par C gene and an Ri ori as replication origin. The vector is capable to integrate a clone plasmid of a circular genome library with lox site by cre enzyme, in a host, E. coli or Agrobacterium.

The present invention is also a binary vector for plant transformation comprising multi-cloning site sandwiched by with a promoter and a terminator for plants in a T-DNA region, and an Ri ori as replication origin.

The present invention further is a genomic library having the ability to transform plants. Each clone constituting the genomic library having the ability to transform plants has an insert in the T-DNA region of the high capacity binary shuttle vector of the present invention.

The present invention is complementation method for assessing the function of genes in a genome fragment inserted in a clone of a genome library. This method comprises introducing said plasmid with a genome insert into an Agrobacterium cell, and transferring said plasmid into a plant. Furthermore, the present invention is another complementation method for assessing the function of genes in a genome fragment inserted in a clone of a genome library. This method comprises integrating a component plasmid of a library with a genome insert and a binary vector as described in claim 8, wherein said library is constructed by using a circular vector with lox site and has E. coli as a host, introducing said integrated vector into an Agrobacterium cell, and then transferring said integrated vector into a plant.

The present invention is a gene obtained with the complementation method described above.

The present invention is a screening method for a useful gene by using the above-mentioned high capacity binary shuttle vector or the library integrating vector.

Furthermore, the present invention is a transformed plant with said high capacity binary shuttle vector. The plant to be transformed includes all kinds of plants, mainly seed plants, and particularly monocotyledonous plants.

The present invention is a method for producing a high efficiency Agrobacterium strain with recA⁻ to maintain stably the binary vector with a large insert. This method comprises generating high transformation efficiency recA⁻ strains by the site-directed mutation on recA gene of said strain to transform to a recA⁻ strain, introducing a homologous recombination to the strains with recA⁺ genes, between the transformed recA⁻ vector and recA⁺ gene in the cell, selecting the recombinant by making replica of the plate on which the strains are spread, and irradiating the plate to screen a clone which can not grow under UV irradiation. Or such recA⁻ strain can be selected by replica after normal mutagenesis and selection under UV irradiation.

The present invention is a high transformation efficiency Agrobacterium strain with recA⁻, wherein said strain can maintain stably the said high capacity binary vector with large insert, and can transform various normally recultitrait plants for transformation.

BRIEF DESCRIPTION OF THE DRAWINGS

FIGS. 3A and 3B show Southern blot analysis of the two genome fragments of about 40 kb, which are introduced into the rice plant by pBIGRZ. A: No deletion or almost no rearrangement of the fragments occurred during transformation as shown by the primary transformants(R₀) as compared with control. This result shows that the genome fragments are intactly transferred to plant cells and stably maintained. B: In the first generation of the progeny(R₁), also no deletion nor rearrangement of the fragments were observed. The result shows that the genome fragments integrated into the plant genomes are stably inherited to their progenies.

This indicates that a genome library usable for complementation tests is actually constructed using this vector. The average insert size was obtained by subtracting the vector size which is about 20 kb from the size of each band on the lane. Two lanes on the right side of the gel are size markers.

Figure 6A:
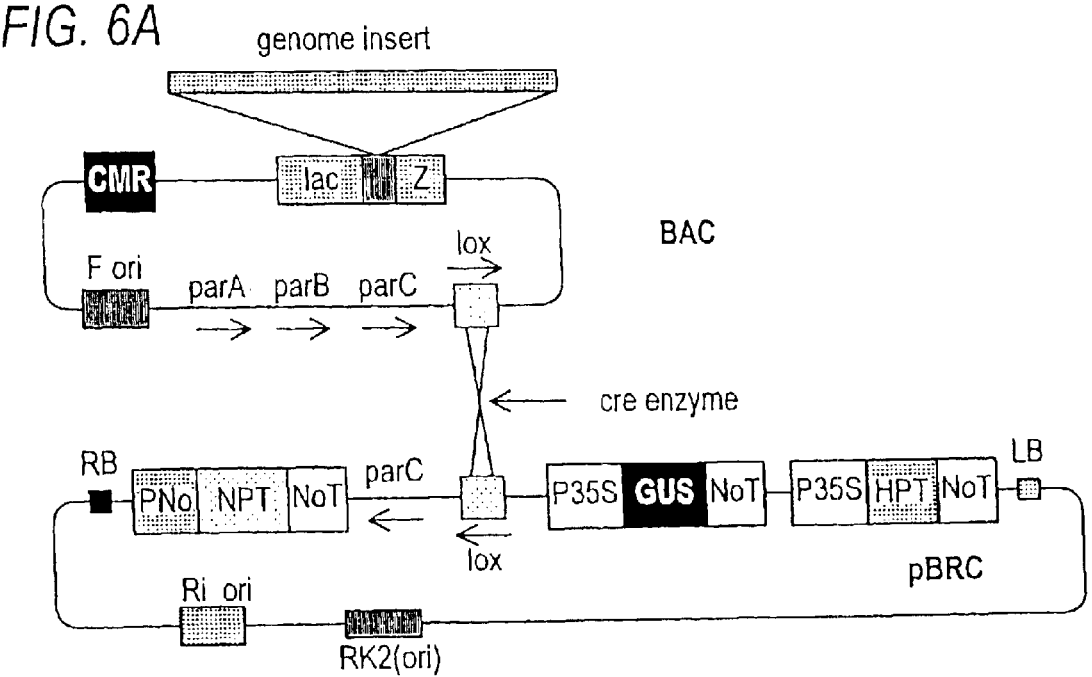
Figure 6B:
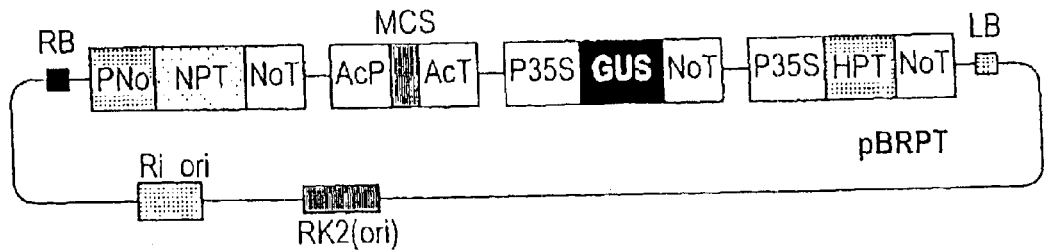

FIGS. 6A and 6B show various inducible vector utilized properties of the high capacity binary shuttle vector of the present invention.

A: a single vector generated by site-directed recombination based on transient cre enzyme expression at lox site. In order to generate this vector, pBRC: one example of a vector to perform complementation test and BAC vector having genome insert and lox site was integrated by transient expression of cre enzyme in host cells. Unintegrated pBRC with BAC is quickly removed when par C sequence is present in it.

B: an example of the vector, pBRPT. This vector is used for introducing a single gene with an expression property from a promoter and terminator, and having a high transformation efficiency of the high capacity vector of the present invention.

DETAILED DESCRIPTION OF THE INVENTION

Hereinafter, the present invention is described in more detail.

The high capacity binary shuttle vector of the present invention was constructed in the following procedure.

Figure 1:
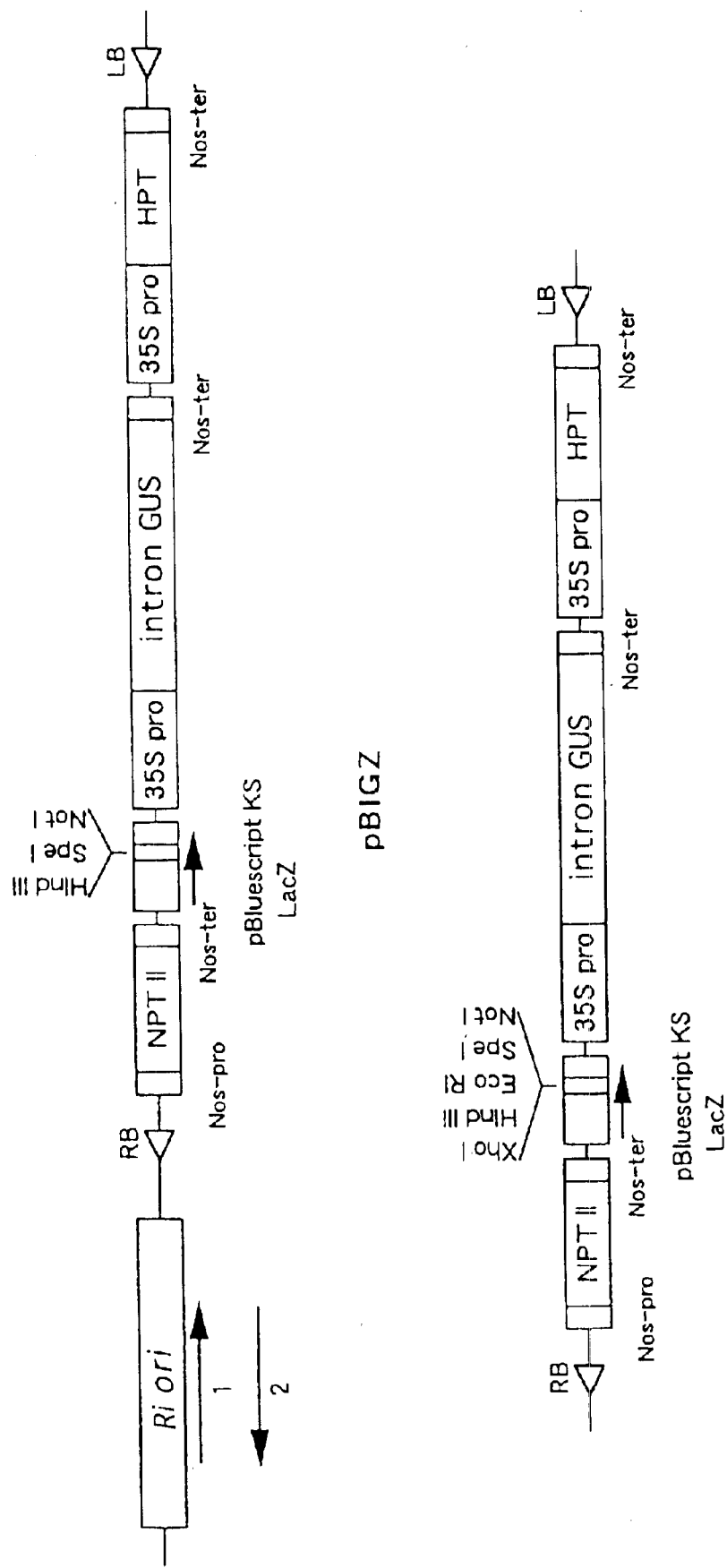
FIG. 1 shows the construct of a high capacity shuttle vector pBIGRZ with Ri ori and similar vector pBIGZ without Ri ori. Construct of the high capacity binary vector pBIGRZ. Arrows of RI ori indicate the direction of the gene and corresponding numbering of the plasmid. Restriction enzymes with the unique cloning site are indicated. RB: right border of T-DNA, LB: left border of T-DNA, NPTII: neomycin resistance gene, NP and NT: Promoter and Terminator of nopaline synthetase, lacZ: β-galactosidase gene, MCS: multicloning site, P35S: 35S promoter, iGUS: β-glucuronidase gene with an intron, HPT: hygromycin resistance gene, Ri ori: replicator origin of Ri plasmid.
Figure 2:
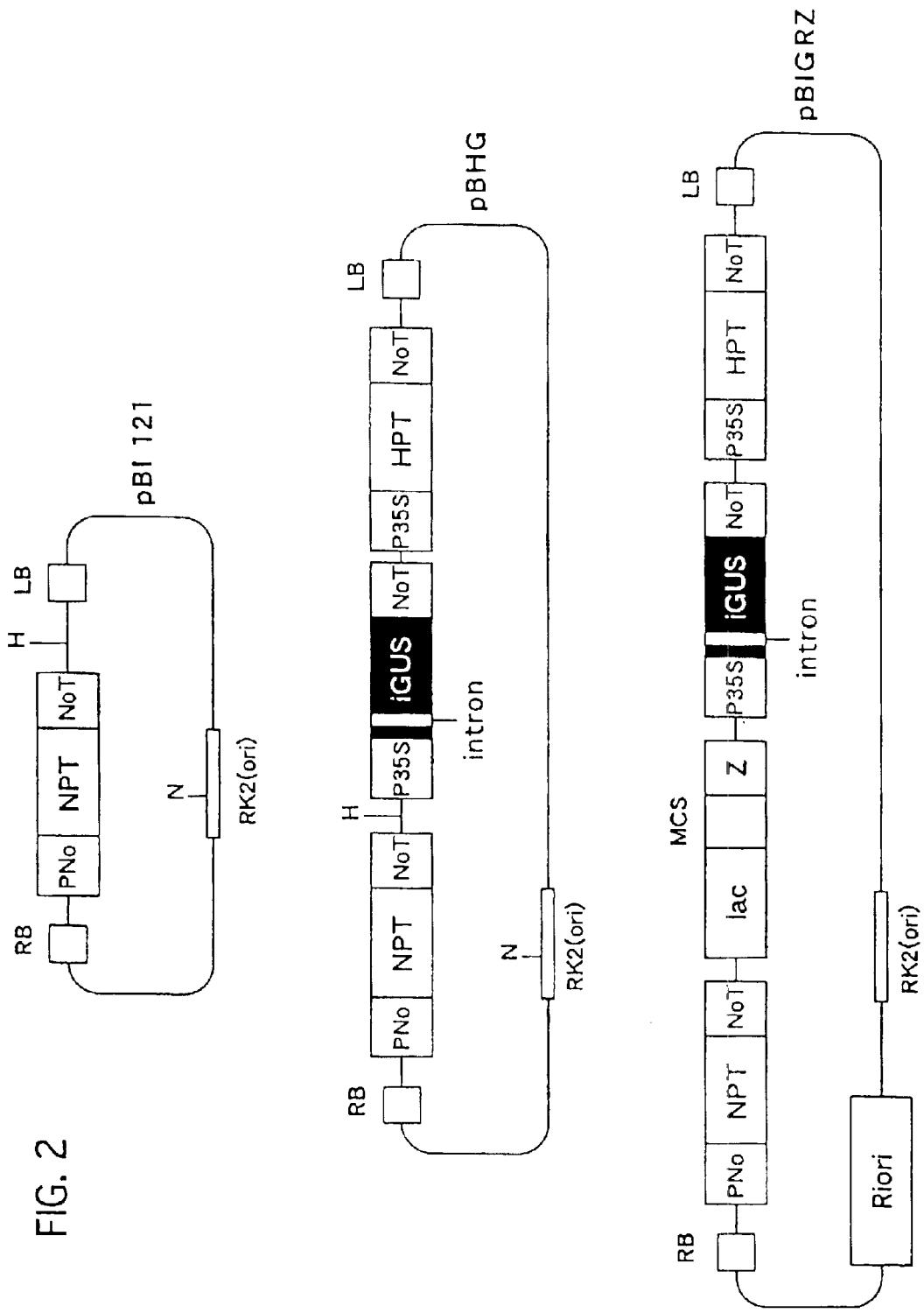
FIG. 2 shows a construction process pBIGRZ from pBI121 and pBIHG.
Figure 4:
FIG. 4 shows flowers and panicles of the rice plant into which a human genome fragment of about 40 kb was introduced by pBIGRZ. The rice plant has excellent fertility, and its heads bend down by the weight of seeds.
Figure 5:
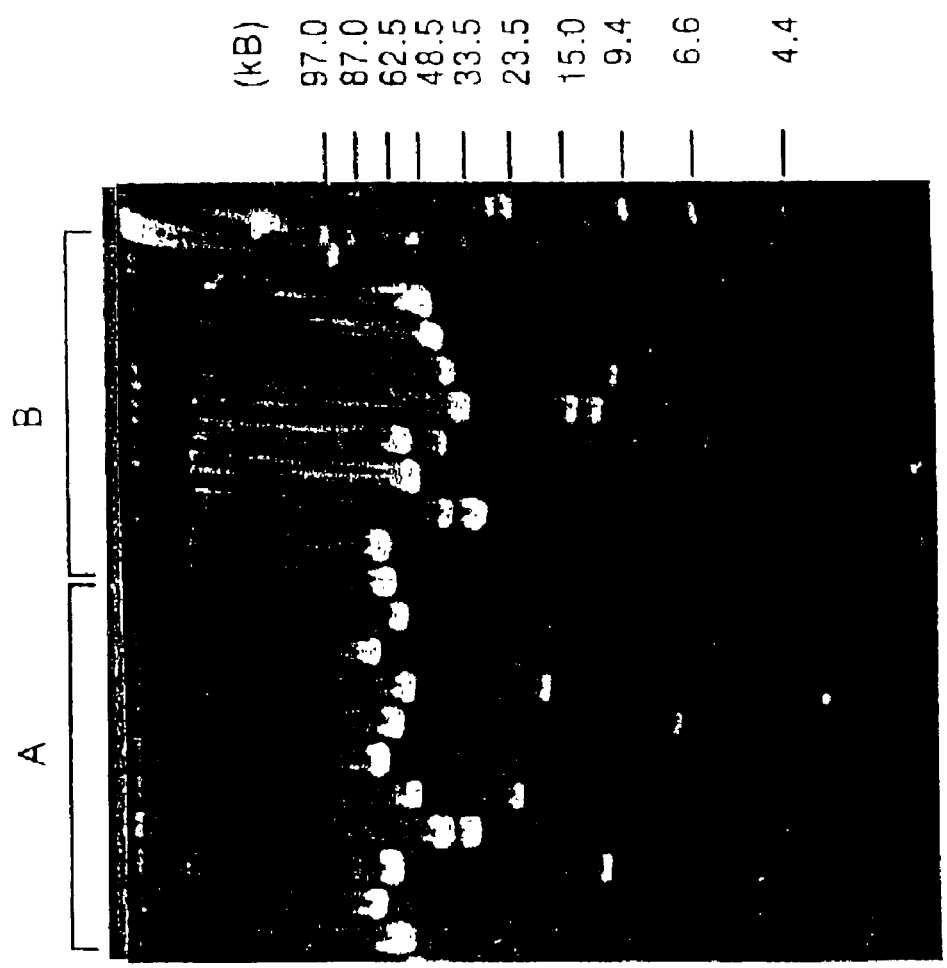
FIG. 5 shows the rice genome library generated using pBIGRZ. They were digested by the restriction enzyme NotI. A shows those in which the genome fragments with 45 kb or larger size were introduced. B shows those in which the fragments with 30 to 50 kb were introduced. In A and B, the average size of the introduced fragments were 51 kb and 39 kb, respectively.

(1) Strategy of a Binary Vector Capable of Stably Maintaining a Large Genome Fragment as an Insert (See FIGS. 1 and 2).

A binary vector system comply with the following requirements are used as the base:

(i) A vector with a T-DNA region, having various genome fragments which are introduced in it as inserts. This T-DNA region can be efficiently introduced into various plant cells.
(ii) A genomic library is constructed easily and stably.
(iii) Plasmid DNA is also prepared easily and E. coli can be used as a host cell.
(iv) The constructed plasmid can be easily transduced into Agrobacterium and maintained stably, to make efficient transformation of plants possible.

As described above, the high capacity binary shuttle vector of the present invention has a requirement that it can be transduced into Agrobacterium.

Agrobacterium tumefaciens is a soil bacterium having Ti plasmid of about 200 kb in size, and on the Ti plasmid has a 10 to 20 kb region called T-DNA. When a plant is infected with Agrobacterium, the T-DNA region is excised by the action of a gene product of vir (virulence) region on Ti plasmid from Agrobacterium. It is known that the T-DNA thus excised is transferred into a plant cells and finally integrated in nuclear DNA of them.

In this case, the T-DNA region and vir region may be included in separate vectors. Therefore, it is possible to construct a binary vector consisting of the T-DNA region, at least one origin of replication which can work in *E. coli* and Agrobacterium and a marker gene only.

The transfer and integration of T-DNA require only 25-bp border sequences located at both ends of T-DNA, and none of the other gene groups located in T-DNA is required. The border sequences located at both ends of T-DNA are called left border (LB) and right border (RB), respectively.

Various binary shuttle vectors comply with the above requirements can be used as the base of construction, as long as it can be used even in the two or other microorganisms as the host when it has proper replication origin, and function as a binary vector. For example, pBI system vectors such as pBI101 and pBI121 are commercially available, and can be conveniently used.

The replication origin used in the pBI binary vector is generally RK2. However, if RK2 is used as the replication origin, often large inserts of 10 kb or larger size are not maintained stably in *E. coli* or Agrobacterium. And its high copy number may lead to mutual recombination making the plasmid instable. Therefore, the vector should be devised to have high capacity for large insert and stability in any of the hosts. By introducing Ri as the low copy number replication origin from Rizobium bacteria, the vector was probed to have high capacity and stability by us. In this case, the Ri ori may be included in the vector singly or together with RK2.

The selection marker for the vector plasmid includes various kinds of antibiotic resistant genes, specifically kanamycin resistance gene (NPT), hygromycin resistant gene (HPT), gene and so forth are used. These markers can be introduced on necessity into the plasmid in the known procedure.

Although a basic vector plasmid in the pBI system has only a kanamycin gene as the selection marker in the host plant, hygromycin resistant gene was additionally introduced. This is because kanamycin does not work well in rice as a selection marker.

Some restriction sites which interfere the multiple cloning site were removed or modified. For example, an EcoRI site in said hygromycin resistant gene was modified so as not to be digested with the restriction enzyme.

The genome or DNA fragments to be introduced into said binary vector can be obtained using known method from any kind of organism including various microorganisms, filamentous fungi, protozoan, animals and plants.

Any DNA or genome fragments of at least about 40 kb or more in size can be introduced into the binary vector and selected depending on the object. As the transformation of rice with 40 kb genome fragment was done without any difference of efficiency from a few kb of gene, it will be possible to introduce larger fragments without difficulty.

It is preferable to introduce cloning sites in a marker gene to check for the introduction of genome fragment. As the marker genes a lacZ (β-galactosidase) gene with cloning sites such as HindIII, SpeI, NotI can be used.

The following genes can be further introduced into the vector, that is, genes to monitor the introduction and expression of the T-DNA in a transformed plant with the binary shuttle vector.

The NPT or HPT genes can be used as such marker genes. β-glucuronidase (GUS) gene is particularly suited to visualize the localized expression sites. Intron-containing GUS (iGUS) is expressed in only eukaryte cells including plant cells, but not in prokaryote cells such as Agrobacterium. Therefore by using intron-containing GUS as the expression marker the noise from the contaminating Agrobacterium can be eliminated.

However, introduction of many makers can adversely affect the expression of the genes of the interest, such markers in the vector should be kept as few as possible.

(2) Introduction of the Genome Fragment into the Vector and Transformation of *E. coli*

(i) Introduction of an Desirable DNA Fragment into the Vector

The vector obtained in (1) above, and fragment DNAs (genome fragments) with suitable size are ligated to the vector using commercially-available ligase, etc. The resulting reaction product is introduced into *E. coli* DH10B cells by electroporation. The cells are then plated onto an LB agar plate containing kanamycin or hygromycin B (50 μg/ml), X-gal and IPTG (isopropyl thiogalactoside). Under usual conditions, the plates are incubated overnight and white colonies formed on the LB agar plate are selected as the transformants in which the above DNA fragment is integrated as an insert.

(ii) Preparation of a Genomic Library by the Transformation Vector

Suitable restriction enzymes, most cases HindIII were used optionally to digest partially or completely the genomic DNA from plant cells or other materials. The fragments thus obtained are separated based on their sizes by CHEF (contour-clamped hexagonal electric field) gel electrophoresis. The DNA fragments thus obtained are ligated to the vector in (1) above. The resulting products are introduced by electroporation into *E. coli* DH10B cells, and the cells having the above DNA fragment as the insert are plated and selected in the same procedure as in (i) on an LB agar plate containing kanamycin (25 μg/ml) or hygromycin B (50 μg/ml), X-gal and IPTG.

(3) Transfer of the Vector from *E. coli* to Agrobacterium

The vector with a insert can be prepared from *E. coli* and can be transferred to Agrobacterium by electroporation method or triparent method (triparent mating method).

(i) Electroporation Method

The binary vector with a insert is recovered from *E. coli* by using the conventional mini-prep method with alkali. If an automatic plasmid extractor is available, a large number of vectors can be extracted efficiently and very easily.

As the recipient Agrobacterium strain of the vector, EHA101 is preferable from its high efficiency. Particularly, rec A⁻ strain which lacks recombinant ability induced from high transformation efficiency strains is suitably employed when large fragments are inserted into those cells. Electro-competent cells are prepared by the known method from Agrobacterium.

The binary vector with a insert recovered by the mini-prep method from *E. coli* is introduced by electroporation into the competent cells of Agrobacterium. The competent cells with the introduced vector are cultured under the same conditions as normal but on the medium containing hygromycin B (50 μg/ml) and kanamycin (50 μg/ml) to select transformants.

(ii) Triparent Method

*E. coli* cells having the binary vector as described in (2) above, *E. coli* cells carrying a helper plasmid, and Agrobacterium cells are mixed and co-cultured to transfer the desired binary vector from *E. coli* to Agrobacterium.

*E. coli* cells carrying the helper plasmid and *E. coli* cells having the introduced binary vector are mixed and co-cultured with Agrobacterium in a suitable medium at 28° C. for 12 to 24 hours.

The suitable medium includes YEP medium etc.

The helper plasmid herein used is defined the plasmid which helps the transfer of a vector from a bacteria into the microorganism of the interest. As examples are pRK2013, etc. If E. coli carrying the helper plasmid is used at the time of co-culture, the vector is efficiently transferred from the binary vector-containing bacteria to Agrobacterium during co-culture.

From the Agrobacterium thus co-cultured as described above, the transformant was selected by combination of kanamycin, tetracycline and hygromycin, and used to transform plants as described below.

(4) Transformation of Plants by Agrobacterium Harboring the Binary Shuttle Vector A plant was transformed by Agrobacterium harboring the binary vector, as follows. The Agrobacterium strain (about $3\times10^8$ to $3\times10^9$ cells/ml) harboring the vector introduced as described above was co-cultured with plant calli or tissue slices in a medium such as 2N6-AS or N6CO at 25 to 28° C. for about 3 days.

As the plant to be co-cultured, seed plants may be used although there is a divergence in the difficulty for transformation. In particular, monocotyledonous plants, which have been difficult to transform so far, that is, rice, wheat, barley, corn and so forth can be included as candidate of recipient. Among them, rice is most preferably used for easiness to regenerate the plant.

After co-culture with the Agrobacterium, the calli or tissue slices are selected in a medium containing suitable antibiotics. If the hygromycin resistant gene was introduced as the selection marker in the binary shuttle vector as described above, the transformed calli are selected by culturing in 2N6-CH or N6Se medium containing hygromycin (10 to 100 $\mu$g/ml) and Cefotaxime (250 $\mu$/ml) or Carbenicilin (500 $\mu$g/ml) to remove Agrobacterium for 1 to 3 weeks.

Re-differentiation of the hygromycin selected calli was induced on the suitable re-differentiation medium such as N6S3-CH, MSre and so forth to give a re-generated plant.

As described above, if the plant cell is transformed by using the binary vector containing the β-glucuronidase gene in T-DNA, the calli or re-generated plants turns blue when x-gluc (x-glucuronide) is added to their media. By this blue color, the successful transformation can be confirmed.

As described above, the high capacity binary shuttle vector of the present invention can be used to introduce a large genome fragment into a plant to transform it.

Therefore, genomic DNA obtained in the standard method from suitable plants or other living things, and digested with suitable restriction enzymes as described above, can be integrated into the high capacity binary shuttle vector of the present invention as described above to prepare a genomic DNA library.

Since the vector of the present invention is a high capacity binary shuttle vector, thus prepared genomic DNA library has the ability to transform various cells. Therefore, this genomic DNA library can be employed to transform other plant cells with the plant DNA fragment contained in each clone consisting of this library.

In particular, the high capacity binary shuttle vector of the present invention can integrate as large DNA or genome fragments more than 40 kb to enable efficient screening useful genes. That is, if a clone which can make complementary transformation of a cultivar or a deficiency mutant, which lacks a certain function, and restore the function the gene of interest must be present in the clone (complementation test).

According to the present invention, the means for introducing a genome fragment of 10 kb or larger size into a higher plant, particularly monocotyledonous crop plants including rice, easily, efficiently and stably under those conditions without rearrangement or deletion and so forth of the genes were established. In addition, the high capacity binary shuttle vector of the present invention can also be used to prepare a genomic library of more than 40 kb in insert size having the ability to transform the plant of the interest. Therefore, this vector is useful for isolating useful genes by using the positional cloning method etc.

Further, since the high capacity binary shuttle vector of the present invention can integrate such a large genome fragment, the high capacity binary shuttle vector of the present invention is also useful for introducing a far larger gene or gene complex efficiently into a plant than the conventional binary vectors.

According to the present invention, the means for assaying genomic functions efficiently by complementation test was established for rice as a crop plants representing the higher plant, particularly monocotyledonous plants. Thus, a group of genes that are biologically important but expressed in a lesser amount, e.g., regulatory genes and genes involved in signal recognition/transduction or genes involved in expression of agriculturally important traits can be isolated considerably easily.

The high capacity was accomplished by using only Ri ori as the replicating origin of the vector.

Furthermore, the efficiency of screening for a useful gene can be drastically improved by using the high capacity binary shuttle vector of the present invention.

This vector can be modified to have a capacity of changing the plasmid with insert of the conventional circular genome library with lox site such as the constituents of a BAC library, into the transformable form for plants.

Up to this time, many genome libraries have been produced, and it is very useful if these libraries can be used for complementation test of plants. The vector having Ri ori alone, or both Ri ori and RK2 ori as its replication origin, for example, the above-mentioned high capacity vector, is very stable in both E. coli and Agrobacterium, and has excellent transformability for the plants. Based on the vector with such properties, the present vector with an Ri ori as the replication origin and a lox site and a par C site in T-DNA regions can be produced. Then, the vector can be introduced together with a circular plasmid, which is constituting a clone of a genome library with a lox site such as BAC library, into an E. coli strain which is engineered to express cre enzyme transiently under a specific condition. The resulting transformants are then subjected to selection by antibiotics of the library vector and then the binary vector. Thus, the vector in which the library component vector such as BAC which has lox site is integrated into lox site in T-DNA region of the another vector is obtained (FIG. 6A).

In the integrated vector obtained hereinabove, the large genome insert is inserted basically as the same manner as in the above-mentioned high capacity binary shuttle vector. Therefore, introduction of the integrated vector into Agrobacterium by using the procedure described above makes the introduction of the inserts into the plants with high transformation efficiency shown in Table I possible. In order to remove the binary vector with Ri ori which was not integrated with the library plasmid, par C sequence is inserted near lox site.

Accordingly, already constructed genome libraries made by vectors such as BAC or P1 having lox site can be utilized for complementation test efficiently without the reconstruction of a library using the high capacity binary vector of the present invention.

As shown in Table 1, the vector with both Ri ori and RK2 ori can efficiently transform the plants markedly than that with RK2 ori alone does. Based on the result, it is expected that the high capacity binary vector can be utilized to transform the plant recalcitrant to gene introduction.

In the vector, pBRGRZ, genes are only introduced as the form of genome fragments or with some promoter and terminator. It is convenient to have a vector with a multi-cloning site between the suitable promoter and terminator to introduce a gene from which the inherent promoter was removed or a full length cDNA to give a desirable expression properties of an arbitrary gene (FIG. 6B). After insertion of the gene or cDNA, such vectors can be introduced into plants for transformation. In general, the combination of actin promoter and actin terminator is preferable to express a gene strongly. It may be avoided that the same promoter or terminator are employed repeatedly in a vector, because it may cause homologous recombination in a host cell.

The high transformation efficiency strain of Agrobacterium with rec A⁻ is produced to maintain a large size plasmid made from the high capacity binary vector of the present invention.

In general, this large plasmid is stably maintained in both E. coli and Agrobacterium, because it is maintained as a single or low copy plasmid. In E. coli, strains with rec A⁻ which can not make genetic recombination, are easily obtained, for example, DH10B. Also in Agrobacterium, some rec A⁻ strains are known. However, as for the high transformation efficiency strains indispensable for transformation of plants which are difficult to transform, there are no report on rec A⁻ strains which is desirable for stable maintenance and transformation of a large plasmid.

Accordingly, such high transformation efficiency rec A⁻ strain is produced by site-directed mutation on rec A gene in EHA101 strain. The mutation is introduced into Agrobacterium by homologous recombination with the chromosomal rec A gene and transformed plasmid with rec A⁻ gene. A plasmid with a rec A⁻ gene produced by site-directed mutagenesis is transformed to a high transformation efficiency Agrobacterium strain and then spread on a plate. After replica plate formation, the replica plate is irradiated by UV, and Agrobacterium cells are then cultured on the plate. Since the mutant with rec A⁻ can not grow under UV, such colonies are selected. When the mutant is used, the clone comprising large genome fragment is more stably maintained in Agrobacterium cells. Such mutant also can be selected by negative selection under UV irradiation as above after normal mutagenesis.

EXAMPLES

Hereinafter, the present invention is described in more detail by reference to examples showing construction of the high capacity binary shuttle vector of the present invention and its application to introduce human genomic DNA into rice. However, the present invention is not limited to the following examples.

Example 1

The high capacity binary shuttle vector of the present invention, pBIGRZ (shown in FIG. 2), was constructed in steps (1) to (3) as follows:

(1) Construction of pBH

A hygromycin phosphotransferase gene (HPT, a gift from Dr. Hatsuyama, Hokkaido University) with a 35S promoter, a nopaline terminator but without EcoRI cleavage site was introduced using ligation into EcoRI site of the left border side (referred to as LB in FIG. 2) in T-DNA of the binary vector pBI121 to construct pBH. In FIG. 2, the 35S promoter and nopaline terminator are referred to as P35S and NPT respectively.

(2) Construction of pBHG

Intron-containing β-glucuronidase (iGUS) was introduced by using standard procedure between HPT and NPT in T-DNA in pBH obtained in (1) above to construct pBHG.

(3) Insertion of the Replication Origin of Ri Plasmid

Ri ori, which is replication origin for Ri plasmid cloned from Rizobium bacteria was inserted by using ligation into NotI site of the outside of T-DNA.

(4) lacZ gene having a multi-cloning site including HindIII, SpeI, and NotI was prepared from the lacZ region in pBluescript and introduced between NPT and iGUS to construct a plasmid, which was designated pBIGRZ.

As described above, since pBIGRZ has a cloning site in lacZ, it can be confirmed whether a fragment from genome and so forth has been inserted in the plasmid in a medium containing X-gal and IPTG.

Example 2

This example shows the introduction of about 40 kb human genome fragment into rice to examine whether the binary-vector pBIGRZ obtained in Example 1 can actually introduce a 10 kb or larger genome fragment efficiently and stably into a monocotyledonous plant.

(1) A NotI site in pBIGRZ in lacZ was digested using a restriction enzyme, and the terminals formed were dephosphorylated. Then human genome NotI fragment DNAs (about 40 kb) which was inserted into 2 cosmids were inserted into the binary vector by ligation. The vector with the insert was introduced into E. coli.

(2) pBIGRZ vector with the introduced human genome fragment was electroporated from the E. coli to Agrobacterium as follows:

The binary vector was recovered from the E. coli by the mini-prep method using alkaline. The prepared binary vector was electroporated into competent cells of Agrobacterium (EHA101) carrying T-DNA-free helper plasmid, and a transformant was selected on a medium containing hygromycin (50 μg/ml) and kanamycin (50 μg/ml).

(3) pBIGRZ vector having the human genome fragment introduced stably into the Agrobacterium was introduced into rice scutellum calli as follows: The Agrobacterium into which the binary vector was introduced was co-cultivated with the calli at 25° C. for 3 days, and the transformed calli were selectively cultured in a hygromycin medium (30–50 μg/ml). Thereafter, their regeneration into plants was prepared in a regeneration medium and then shoot formation was done in a hormone free medium to give re-differentiated plants. After the plants were acclimated, they were grown in pots in a greenhouse.

pBIGRZ1 and pBGRZ2, which has Ri ori with opposite direction, were used to examine whether the direction of Ri ori affects the stability of the plasmid in Agrobacterium (EHA101), transient expression rate of GUS after co-cultivation with rice calli, and regeneration rate of the re-differentiated plants in the above process.

The results are shown in Table 1.

TABLE 1

Effect of Ri ori for the maintenance in bacteria and transformation of rice (cv. Nipponbare) with the plasmids.

| plasmids | insert | maintenance in EHA101* | trangient GUS expression rate after co-culture with EHA101 | Plant regeneration rate plants/ co-cultured cali |
|---|---|---|---|---|
| pBIGZ | Human genome cosmid 78C10 | | | |
| | Eco RI 10 kb fragment | + | 10/12 (83%) | N.T. |
| | Eco RI 30 kb | ± | 0/17 (0%) | 0/60 (0%) |
| | Not I 40 kb | − | N.T. | N.T. |
| | Human genome cosmid 605 | | | |
| | Eco RI 15 kb | + | 6/11 (55%) | 0/52 (0%) |
| | Not I 40 kb | − | N.T. | N.T. |
| | Lambda DNA | | | |
| | Hind III 27 kb | + | 13/17 (76%) | N.T. |
| | Rice BL-1 genome cosmid | | | |
| | Not I 7 kb | + | 10/14 (71%) | N.T. |
| | Not I 7.5 kb | + | 16/19 (84%) | N.T. |
| | Not I 25 kb | − | N.T. | — |
| pBIGRZ 1 | Human genome cosmid 78C10 | | | |
| | Not I 40 kb | + | 6/9 (67%) | 11/83 (13%) |
| | Human genome cosmid 605 | | | |
| | Not I 40 kb | + | 12/13 (92%) | 60/74 (81%) |
| | Rice BL-1 genome cosmid | | | |
| | Not I 7.5 kb | + | 11/14 (79%) | N.T. |
| | Not I 25 kb | + | 7/17 (41%) | N.T. |
| pBIGRZ 2 | Human genome cosmid | | | |
| | Not I 40 kb | + | 8/11 (73%) | 35/78 (45%) |
| | Human genome cosmid | | | |
| | Not I 40 kb | + | 5/8 (63%) | 15/81 (19%) |

* +, ± means ca. $10^6$, $10^4$ clones of DH10B transformed/DNA prepared from 2 ml of EH101 culture.

(4) Simultaneously, the same human genome fragment was introduced into pBIGZ (FIG. 1) and the introduction of this genome fragment into callus cells of rice was attempted in the same procedure as above. pBIGZ is a vector having the same structure as pBIGRZ except that it has only RK2 ori in pBI121 and does not have Ri ori.

The maintenance of the plasmid in Agrobacterium and degrees of regeneration of plants are shown in Table 1.

(5) By comparing pBIGRZ with Ri origin and pBIGZ without it, it was revealed that the stability of the plasmid in Agrobacterium and the plant regeneration rate significantly increased in the plant with pBIGRZ. In particular, the significant increase in the plant regeneration rate was observed in the plant with pBIGRZ.

(6) No significant difference due to the direction of Ri ori in the plasmid was observed in the maintenance of the plasmid in Agrobacterium and the rate of regeneration of plants.

(7) Genomic DNA was extracted from green leaves of the transformed plants and was digested with HindIII. This digested fragment was analyzed by Southern blotting with human genome NotI inserts in cosmids (H78C10, H605) used as probes. The results are shown in FIGS. 3A and 3B.

In FIG. 3, panel A is the results of Southern hybridization of the $R_0$ generation plant transformed with H605 (about 44 kb), or with H78C10 (about 38 kb). In the reference lane in each panel, the digested fragment from the original human genome fragment with HindIII was electrophoresed at a single copy equivalent. Lanes 1 to 10 of each clone show the results of Southern hybridization of HindIII-digested DNA extracted from leaves of one of the regenerated plants. The results by Southern hybridization of the DNA fragment obtained from each transformant showed almost the same pattern as the reference. Panel B shows Southern brot analysis of 3 plant lives which were obtained from the same parent plant. In any plant life, almost single copy of the same fragment as control is harbored. Bands marked with dots are those hybridized to random marker.

Figures 3A, 3B:
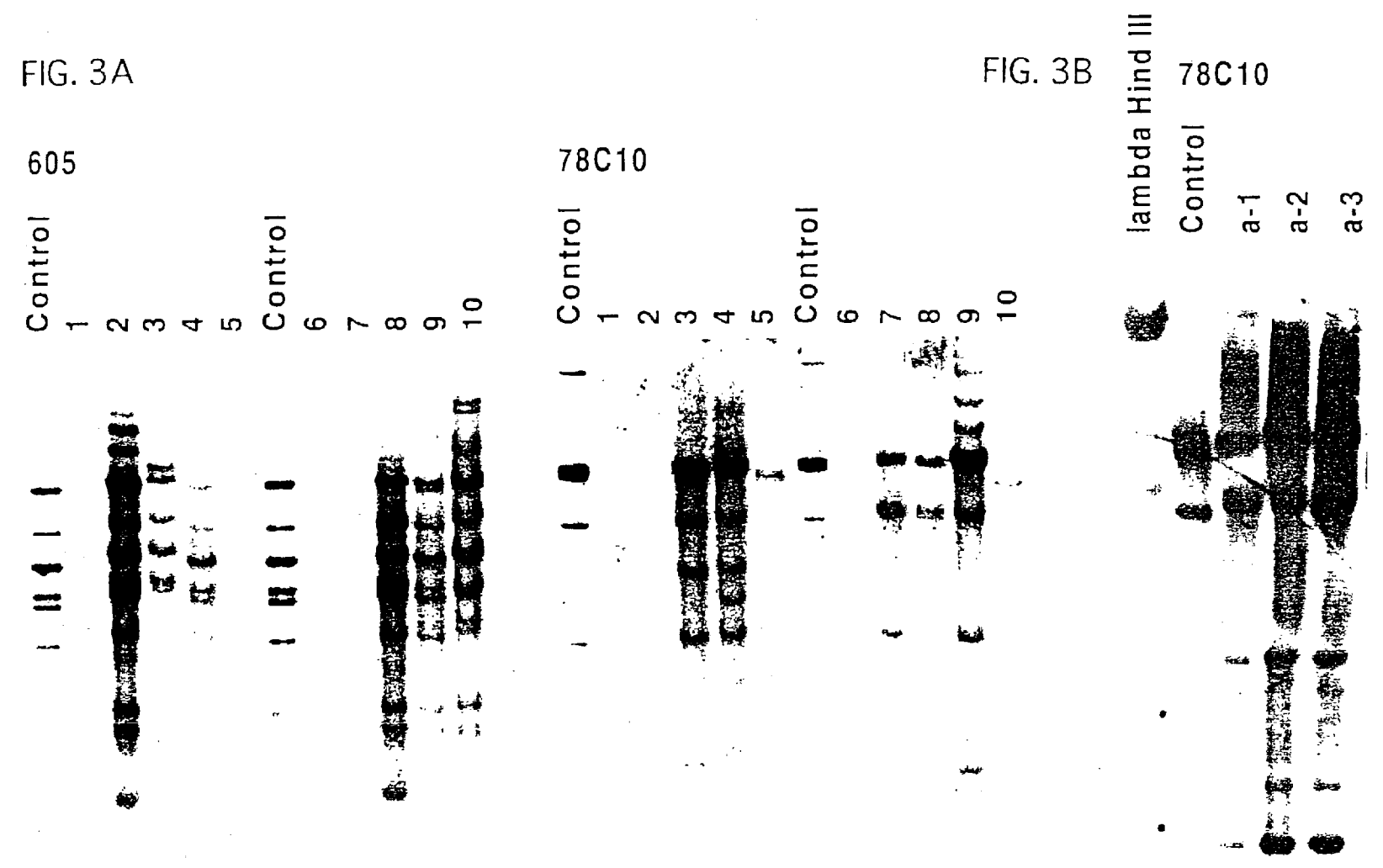

As shown in FIGS. 3A and 3B, it was demonstrated that one or more copies of genome fragments were introduced without rearrangement into the rice genome at 6/10 plants for human cosmid fragment H78C10 and 5/10 plants for fragment H605. Also it was demonstrated that such genome fragments are stably inherited by the offsprings.

As described above, when a large genome DNA fragment was inserted into the vector of the present invention and used for transformation of the plant, the inserted DNA fragment is stably maintained in the vector of the present invention without deletion or rearrangement and introduced efficiently into plant cells. Therefore, it was also demonstrated that the high capacity binary shuttle vector of the present invention is useful for narrowing the target region in the genome by complementing the functions of the gene of the interest with as large a genomic DNA fragment as possible.

In this example, the results of rice transformation were shown. However, based on the previous findings, dicotyledonous plants are generally easier in transformation by Agrobacterium than rice, so the high capacity binary vector of the present invention is expected to be applied to various kinds of dicotyledonous plant, and by little modification of the experimental conditions, it is also expected to apply in the wider range of crop plants including other important monocotyledonous crop plants.

What is claimed is:

1. A method for producing a transformed plant, comprising the step of introducing a binary shuttle vector, which comprises a T-DNA region and Ri ori and RK2 ori as the replication origins and which is inserted with a DNA fragment of 10 kb or larger in the T-DNA region, into a plant.

2. A method according to claim 1, wherein said plant is a seed plant.

3. A method according to claim 2 wherein said plant is a monocotyledonous plant.

* * * * *

UNITED STATES PATENT AND TRADEMARK OFFICE
CERTIFICATE OF CORRECTION

PATENT NO. : 6,794,190 B2
DATED : September 21, 2004
INVENTOR(S) : Shinji Kawasaki It is certified that error appears in the above-identified patent and that said Letters Patent is hereby corrected as shown below:

Title page,
Item [73], Assignee, change "National Institute of Agrobological Sciences" to
-- National Institute of Agrobiological Sciences --.

Signed and Sealed this

First Day of February, 2005

JON W. DUDAS
*Director of the United States Patent and Trademark Office*